United States Patent
Rapino et al.

(10) Patent No.: US 11,920,153 B2
(45) Date of Patent: Mar. 5, 2024

(54) COMPOSITIONS, DEVICES AND METHODS FOR THE CONTROL IN VITRO OF CHEMICAL MICROAMBIENT IN CELL CULTURES

(71) Applicant: Alma Mater Studiorum—Università di Bologna, Bologna (IT)

(72) Inventors: Stefania Rapino, Bologna (IT); Francesco Zerbetto, Bologna (IT); Gastone Castellani, Bologna (IT); Stefano Salvioli, Bologna (IT); Beatrice Fraboni, Bologna (IT); Isabella Zironi, Caselecchio di Reno (IT); Maria Conte, Marzabotto (IT); Claudio Franceschi, Bologna (IT); Daniela Salvatore, Lanciano (IT); Maila Becconi, Nuoro (IT)

(73) Assignee: Alma Mater Studiorum—Università di Bologna, Bologna (IT)

( * ) Notice: Subject to any disclaimer, the term of this patent is extended or adjusted under 35 U.S.C. 154(b) by 444 days.

(21) Appl. No.: 16/339,164

(22) PCT Filed: Oct. 3, 2017

(86) PCT No.: PCT/IB2017/056081
§ 371 (c)(1),
(2) Date: Apr. 3, 2019

(87) PCT Pub. No.: WO2018/065887
PCT Pub. Date: Apr. 12, 2018

(65) Prior Publication Data
US 2019/0300846 A1    Oct. 3, 2019

(30) Foreign Application Priority Data
Oct. 4, 2016 (IT) .................. 102016000099380

(51) Int. Cl.
*C12N 5/00* (2006.01)
*C12N 5/09* (2010.01)
(Continued)

(52) U.S. Cl.
CPC ......... *C12N 5/0018* (2013.01); *C12N 5/0068* (2013.01); *C12N 5/0693* (2013.01);
(Continued)

(58) Field of Classification Search
CPC ........ C12N 9/00; C12N 11/08; C12N 9/0065; C12N 5/0068; C12N 11/04; C12N 5/0693;
(Continued)

(56) References Cited

FOREIGN PATENT DOCUMENTS

| WO | WO-2013134401 A2 | 9/2013 |
|----|------------------|--------|
| WO | WO-2014065863 A1 | 5/2014 |
| WO | WO-2018065887 A1 | 4/2018 |

OTHER PUBLICATIONS

Weltin et al. Cell culture monitoring for drug screening and cancer research: a transparent, microfluidic, multi-sensor microsystemLab on a Chip (2014), 14, 138-146; (Year: 2014).*
(Continued)

*Primary Examiner* — Sean C. Barron
(74) *Attorney, Agent, or Firm* — Sterne, Kessler, Goldstein & Fox P.L.L.C.

(57) ABSTRACT

The present invention relates to compositions comprising a polymeric matrix or a gel containing functional enzymes capable of re-creating under culture conditions the cell microenvironment existing in vivo. The present invention also relates to devices for cell cultures comprising such compositions, in particular hydrogel and the use thereof to control the chemical microenvironment of a cell culture or mimic physiological or pathological conditions of the in vivo cells. The compositions and the devices described
(Continued)

herein could be also used in vitro for evaluating the therapeutic effect of a compound on a determined cell line or on primary cells.

15 Claims, 9 Drawing Sheets

(51) Int. Cl.
| | |
|---|---|
| *C12N 9/00* | (2006.01) |
| *C12N 9/02* | (2006.01) |
| *C12N 9/04* | (2006.01) |
| *C12N 9/08* | (2006.01) |
| *C12N 11/04* | (2006.01) |
| *C12N 11/06* | (2006.01) |
| *C12N 11/087* | (2020.01) |
| *C12N 11/089* | (2020.01) |
| *C12N 11/12* | (2006.01) |
| *G01N 33/50* | (2006.01) |

(52) U.S. Cl.
CPC .............. *C12N 9/00* (2013.01); *C12N 9/0006* (2013.01); *C12N 9/0036* (2013.01); *C12N 9/0053* (2013.01); *C12N 9/0061* (2013.01); *C12N 9/0065* (2013.01); *C12N 9/0069* (2013.01); *C12N 9/0093* (2013.01); *C12N 11/04* (2013.01); *C12N 11/06* (2013.01); *C12N 11/087* (2020.01); *C12N 11/089* (2020.01); *C12N 11/12* (2013.01); *C12Y 101/03004* (2013.01); *C12Y 106/03001* (2013.01); *C12Y 109/03001* (2013.01); *C12Y 110/03002* (2013.01); *C12Y 111/01006* (2013.01); *C12Y 113/12004* (2013.01); *C12Y 117/03002* (2013.01); *G01N 33/5008* (2013.01); *C12N 2500/02* (2013.01); *C12N 2501/71* (2013.01); *C12N 2533/30* (2013.01); *C12N 2533/50* (2013.01); *C12N 2533/54* (2013.01); *C12N 2533/70* (2013.01); *C12N 2533/72* (2013.01); *C12N 2533/74* (2013.01); *C12N 2533/76* (2013.01); *C12N 2533/78* (2013.01); *C12N 2533/80* (2013.01); *C12N 2537/10* (2013.01)

(58) Field of Classification Search
CPC .. C12N 5/0018; C12N 9/0036; C12N 9/0069; C12N 9/0006; C12N 9/0053; C12N 9/0093; C12N 11/087; C12N 11/089; C12N 11/12; C12N 11/06; C12N 9/0061; C12N 2533/72; C12N 2533/78; C12N 2533/50; C12N 2533/70; C12N 2501/71; C12N 2533/74; C12N 2533/76; C12N 2537/10; C12N 2533/54; C12N 2533/30; C12N 2500/02; C12N 2533/80; C12Y 111/01006; C12Y 110/03002; C12Y 117/03002; C12Y 101/03004; C12Y 113/12004; C12Y 109/03001; C12Y 106/03001; G01N 33/5008

See application file for complete search history.

(56) References Cited

OTHER PUBLICATIONS

Yu et al. Effects of Omega-3 Fatty Acids on Apoptosis of Human Gastric Epithelial Cells Exposed to Silica-Immobilized Glucose Oxidase. N.Y. Acad. Sci. (2009), 1171, 359-364 (Year: 2009).*
Cheng et al. Optimizing the design and in vitro evaluation of bioreactive glucoseoxidase-microspheres for enhanced cytotoxicity against multidrug resistant breast cancer cells. Colloids and Surfaces B: Interfaces (2015), 130, 164-172 (Year: 2015).*
Liu et al. Scanning electrochemical microscopy of living cells: Different redox activities of nonmetastatic and metastatic human breast cells. PNAS (2000), 97(18), 9855-9860 (Year: 2000).*
Mok et al. Superparamagnetic iron oxide nanoparticle-based delivery systems for biotherapeuticsExpert Opin Drug Deliv. (2013), 10(1), 73-87; (Year: 2013).*
Misun et al. Multi-analyte biosensor interface for real-time monitoring of 3D microtissue spheroids in hanging-drop networks. Microsystems and Nanoengineering (Jun. 2016), 2, 16022, 9 pages (Year: 2016).*
Crowley-Weber et al. Development and molecular characterization of HCT-116 cell lines resistant to the tumor promoter and multiple stress-inducer, deoxycholate. Carcinogenesis (2002), 23912), 2063-2080. (Year: 2002).*
Dawes et al. Enzyme-immobilized hydrogels to create hypoxia for in vitro cancer cell culture. Journal of Biotechnology (Mar. 2017), 428, 25-34. (Year: 2017).*
Zawko et al. Simple benchtop patterning of hydrogel grids for living cell microarrays.Lab on a Chip (2010), 10, 379-383. (Year: 2010).*
Buenger, D, et al., "Hydrogels in sensing applications," Progress in Polymer Science 37(12):1678-1719, Elsevier, Netherlands (2012).
Grist, S.M., et al., "Optical Oxygen Sensors for Applications in Microfluidic Cell Culture," Sensors 10(10): 9286-9316, MDPI, Switzerland (2010).
He, C., et al., "A novel stable Amperometric glucose biosensor based on the adsorption of glucose oxidase on poly(methyl methacrylate)bovine serum albumin coreshell nanoparticles," Sensors and Actuators B: Chemical: international Journal Devoted to Research and Development of Physical Transducers 166:802-808, Elsevier, Netherlands (2012).
International Search Report and Written Opinion for International Application No. PCT/IB2017/056081, dated Jan. 3, 2018, European Patent Office, Netherlands, 18 pages.
Brown, J.Q., et al., "Encapsulation of glucose oxidase and an oxygen-quenched fluorophore in polyelectrolyte-coated calcium alginate microspheres as optical glucose sensor systems," Analyst 135(10):2620-2628, Royal Society of Chemistry, England (2010).
Rocchitta, G., et al., "Analytical Problems in Exposing Amperometric Enzyme Biosensors to Biological Fluids," Sensors 16(6):780, MDPI, Switzerland (2016).

* cited by examiner

COMPOSITIONS, DEVICES AND METHODS FOR THE CONTROL IN VITRO OF CHEMICAL MICROAMBIENT IN CELL CULTURES

TECHNICAL FIELD OF THE INVENTION

The present invention relates to compositions comprising a matrix containing functional enzymes capable of re-creating, under culture conditions, the cell microenvironment existing in vivo. The present invention also relates to devices for cell cultures comprising such compositions, in particular hydrogel compositions, and to the use thereof to control the chemical microenvironment of a cell culture or mimic physiological or pathological conditions of in vivo cells. The compositions and the herein described devices could also be used in vitro to evaluate the therapeutic effect of a compound on a determined cell line or on primary cells.

STATE OF PRIOR ART

The oxygen levels and the mechanical properties are the fundamental parameters for the cell growth, parameters which regulate all functions and decisions belonging to a cell. Such properties have to be controlled perfectly in in vitro cell cultures. The in vitro cell cultures generally are performed with 20% oxygen which is not the oxygen concentration found in the in vivo tissues corresponding to about 5% according to tissues and conditions. The glucose, oxygen and pH gradients differ considerably between the cell cultures and the typical conditions of crucial anatomical districts such as the stem-cell niches, the solid tumour masses, the senescent tissues. The devices which re-create in a simple, inexpensive and controllable way the main physiological conditions (in primis the oxygen gradient, glucose and pH) existing in the tissues and in in vivo cell environments, conditions which cannot be obtained with the common in vitro culture techniques unless by using specific instrumentation (for example hypoxidic hoods), with complicated methods and high costs, are not disclosed in the state of art.

The oxygen, under physiological conditions, has partial pressures varying between 24 and 160 mmHg relatively to the involved organ or tissue. On the contrary, under pathological conditions, in particular the tumour ones, the oxygen levels inside the tissues decrease drastically or, in the most dramatic cases, are null, these two circumstances are defined hypoxic and anoxic, respectively, which then are to be distinguished from the normoxic conditions: synonym of physiological. The two main causes of this strong decrease lie in the wide disorganization of the blood vessels which are not capable of sustaining the adequate input of oxygen to the tissues and the frequent formation of hemoglobin intermediaries dangerous for the organs, such as carboxy hemoglobin and methaemoglobin; the partial pressures in this case range from 0.02 mmHg around the intracell cytochromes to 45 mmHg related to the oxygen levels in the blood capillaries.

The difference between in vitro culture conditions and the in vivo real conditions, both under physiological and pathological conditions, represents a problem existing in all pre-clinical experiments, in the drug discovery processes, in the study of diseases, in the regenerative medicine, in the experimentation of drugs and in the customized treatment.

The patent application US2015362483 describes a method for mimicking in vitro both pathological and physiological in vivo cell conditions. The method requires a device with a mechanical component, which is expensive and difficult to be managed, surely which cannot be multiplied at the level of the culture plates commonly used for the cell growth. The micrometric check of the concentrations and the gradients of the metabolites and of the soluble molecules in the extracell matrix is not reached as required to reproduce physiological conditions.

Therefore the problem is much felt to provide new methods, compositions and devices for mimicking in vitro effectively the physiological or pathological cell conditions which do not show the disadvantages of the solutions described in the prior art.

SUMMARY OF THE INVENTION

The present invention is based upon the use of compositions, in particular in form of hydrogel, comprising matrixes containing functional enzymes capable of re-creating, under culture conditions, the cell microenvironment existing in vivo.

The authors of present invention have showed not only that the cell culture environment can be controlled by the herein described compositions and hydrogel, but also that the conditions which one succeeds in creating are very similar to those existing in a tissue, both normal and tumour tissue. The invention results to be advantageous since the use of the devices comprising the composition and the hydrogels allows to reproduce in vitro the specific physiological conditions and to study the relative cell metabolism, for example the effects of the environment on the metabolism, the cell signaling, the gene expression, both of healthy and tumour cells; moreover it allows to estimate the tumour growth factors and, based thereupon, to devise more effective therapeutic strategies. The devices according to the present invention represent unique systems for pre-clinical investigations, as reliable as the in vivo systems but with all advantages of the in vitro systems. The applications can be several, from the experimentation of new drugs to evaluate the potentiality thereof to the development of new therapeutic strategies, with the advantage of working on the real tumour microphysiological environment. Besides, with computational methods it would be possible to develop new strategies of drug delivery, by taking into account of the concentration gradient naturally present in the human tissues and test them in these biomimetic systems.

Firstly, the present invention then relates to compositions to be used in in vitro cell cultures characterized in that they comprise a matrix, in particular a polymeric or protein matrix, containing one or more enzymes capable of catalysing the reduction of oxygen to which the oxygen gradient in said cell cultures is controlled.

Secondly, the present invention relates to a device for cultivating in vitro cells comprising a container for cells and the compositions according to anyone of the herein described embodiments.

Additionally, the present invention relates to a in vitro method for mimicking physiological or pathological conditions of in vivo cells characterized by a step of cultivating a cell line (or primary cells) in a container for cells wherein a composition or hydrogel according to anyone of the herein described embodiments has been deposited. Additionally, the present invention relates to a method for controlling the chemical microenvironment of a cell culture characterized by a step of cultivating a cell line (or primary cells) in a container for cells wherein a composition according to anyone of the herein described embodiments has been deposited.

Additionally, the present invention relates to a method for evaluating the effect of a drug or a compound for a determined physiological or pathological condition comprising a step of cultivating a cell line in a container for cells wherein a composition according to anyone of the herein described embodiments has been deposited and a step of adding said drug or compound on said cell line.

Additionally the present invention relates to a method for preparing the compositions in form of hydrogel comprising the following steps:
a) preparing a solution comprising one or more enzymes apt to catalyse the reduction of oxygen;
b) adding a cross-linking agent;
c) gelling the solution.

BRIEF DESCRIPTION OF THE FIGURES

FIG. 1 shows schematically the operation of the device according to the present invention.

DETAILED DESCRIPTION OF THE INVENTION

Figure 1:
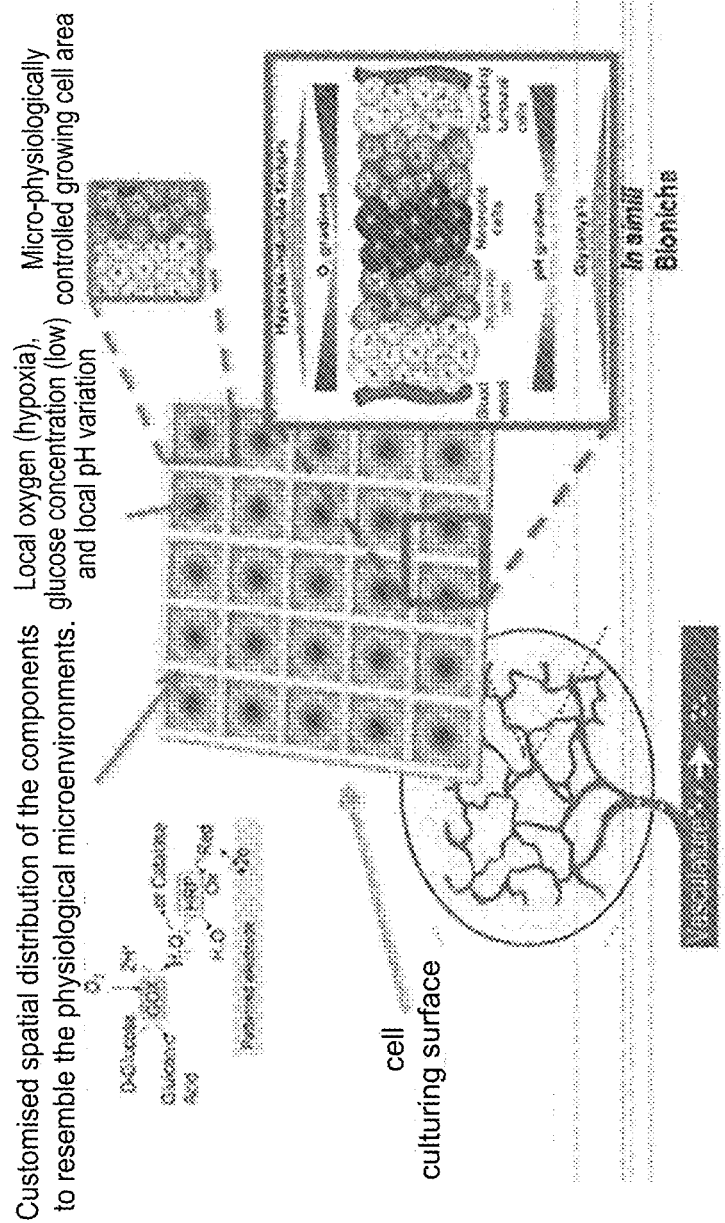
FIG. 1.
Figure 2:
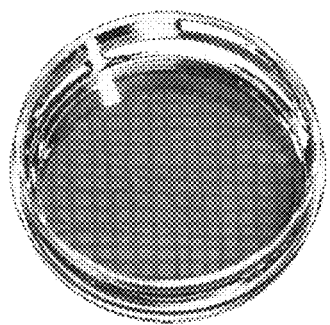
FIG. 2: photo of a prototype of culture plate modified by a grid of the active matrix to re-create the tumour microenvironment.

The present invention relates to compositions comprising a matrix containing functional enzymes capable of re-creating under culture conditions the cell microenvironment existing in vivo. In particular it relates to polymeric matrixes and hydrogel to be used in in vitro cell cultures characterized in that they comprise one or more enzymes capable of catalysing the reduction of oxygen in the cell culture so as to control the oxygen gradient.

In the present description under the term "to be used in cell cultures" they are meant to be suitable to be used with cell cultures, in particular eukaryotic cell cultures and more in particular human cell cultures. To belong to this definition then biocompatible compositions or hydrogels are meant, more in detail which do not form toxic products for the cell.

In the present description under the term "matrix" and "polymeric matrix" compounds of hydrogel, matrigel, polymers capable of incorporating or absorbing/adsorbing the active enzymes are meant, moreover under "matrixes" substances are meant which, once deposited on a suitable substrate (for example the plastic of the culture plates), are capable of linking firmly the enzymes thereto so that they could perform their function in producing the gradient, under the term 'matrixes' the composition resulting from these substances with the enzymes themselves is then meant. The term "matrix" is used in case gels are used (for example protein-based gels) or substances capable of absorbing/adsorbing/binding covalently the enzymes, "polymeric matrixes" in case said matrixes consist of polymeric structures.

The enzymes included in the matrixes of the herein described compositions and of the hydrogels could be enzymes which consume $O_2$ without forming toxic products for the cell, the herein described matrixes could include even a second enzyme which removes/consumes the toxic product produced by the first enzyme.

Furthermore, the enzymes should be active in the cell culture for a period of time sufficient for cultivating the cells for example 12, 24, 48 or 72 hours, in other words the enzymes should not be in denatured form inside the hydrogel, but in their catalytically active form.

As explained in the summary of the invention and in the section of the examples and experimental data the activity of consuming oxygen by the enzymes allows to control the oxygen gradient in the in vitro cell cultures.

The matrix could be prepared based upon different principles of interaction between the enzymes and the matrix, for example crosslinking with glutaraldeide, trapping in polymeric matrix, adsorption by physical or electrostatic interactions. The first two methods are those most used for immobilizing an enzyme. The crosslinking is a process based upon the formation of covalent bonds between two or more molecules whereas trapping in polymeric matrix is based upon purely mechanical and electrostatical principles. Examples of agents for the cross-linking are for example glutaraldehyde (GDA), Bis(sulfosuccinimidyl) suberate BS3, N-hydroxysuccinimide, formaldehyde, use of photoreactive agents in combination with UV.

According to a preferred embodiment the composition is in form of hydrogel, for example for trapping the enzymes silicone hydrogels, polyacrylamides, cellulose, cellulose derivatives, collagen, carboxymethylcellulose, alginate, chitosan, agar, polimacon, hyaluronic acid, polymethylmethacrylate, hydrogel peptide-mimetics could be used, wherein the enzymes are associated to the matrix with crosslinking agents or mechanically trapped after the matrix crosslinking.

Examples of enzymes catalysing the reduction of oxygen are Glucose oxidase (GOx), Laccases, NADPH oxidase, xanthine oxidase, lactate oxidase, cytochrome oxidase, any oxidase and oxidoreductase using oxygen as substrate.

According to a preferred embodiment the composition, preferably in form of hydrogel, will include Glucose oxidase and Catalase enzyme. Glucose oxidase—GOx—is an enzyme of the family of oxidoreductases which catalyses the following reaction:

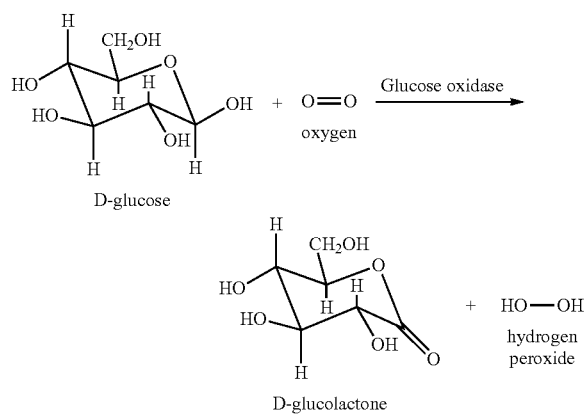

Hydrogen peroxide is a very reactive molecule, toxic for cells, for this reason the above reaction was coupled to that of Catalase—CAT—, another very important oxidoreductase in the biological systems, which transforms the ROS species produced in water. Net of both reactions two oxygen molecules are transformed into two molecules of water plus one of oxygen, which will return into the cycle of Glucose oxidase. The hydrogel consumes oxygen in presence of glucose, the glucose is present in cell culture means as fundamental substrate of the cell metabolism. This preferred embodiment then has several advantages. Glucose oxidase in solution will tend to gel quickly. Glucose oxidase will be for example the one purified from fungus *Aspergillus Niger* or other sources, whereas Catalase could be purified for example from bovine liver. Glucose oxidase uses the oxygen to oxidize the glucose, such reaction then, apart for providing the use of a "sacrificial" substrate naturally and physiologically existing in the cell culture means, allows to control even the concentration of local glucose and the gradient thereof (see the Diagram shown in FIG. 1). Even the pH can be controlled in the same way as the product of the glucose oxidation is an acid. Several oxidases and enzymes can be used at the same time, in the same preparation, to vary in controlled and independent way the local concentrations of glucose, oxygen and pH.

In the same way other enzyme peroxidases can be used to remove catalytically the hydrogen peroxide produced in the oxygen reduction reaction, for example Horseradish peroxidase (HRP) can be used.

The concentrations of enzymes to be used in the preparations can be provided by means of simulations which use the master equation or by means of finite element simulations in order to obtain specific local concentrations and gradients in the cell culture environment. According to an embodiment the hydrogel could further comprise the Bovine Serum Albumin (BSA). In the gel formation the use of a solution of Bovine Serum Albumin (BSA) as protective matrix resulted to be advantageous to avoid the denaturation of the enzymes during gelification. Moreover, BSA existing in huge concentrations enters the hydrogel network, it constitutes it and creates many cross-links among the BSA molecules, and between BSA molecules and enzyme molecules: in this way the concentration of the enzymes can be reduced or increased to the quantities required by the device without the risk that the enzyme is not fixed in the gel if existing at very low concentrations, moreover the presence of BSA decreases the probability of intermolecular cross-links in the enzymes which could denature them by inhibiting the activity thereof.

The present invention also relates to devices suitable to cultivate in vitro cells comprising a container for cells and the compositions and the hydrogels described above, in particular with the polymeric matrixes containing the active enzymes according to anyone of the herein described embodiments. With the device any container could be used suitable to cultivation of cell lines such as for example Petri dishes or other containers available on the market. The device could provide that the hydrogel is deposited as one single or multiple layer on the bottom of the container for cells.

According to an embodiment in the device the polymeric matrix with the enzymatically active components will be used, encapsulated in (magnetic or not) microspheres.

According to an embodiment the hydrogels cold be prepared with a process comprising the following steps:
   a) preparing a solution comprising one or more enzymes capable of catalysing the reduction of oxygen;
   b) adding a cross-linking agent;
   c) gelling the solution.

Preferably the method will comprise the addition of BSA followed by the addition of a cross-linking agent such as for example glutaraldehyde (GDA). The enzymes and the BSA preferably will be mixed in buffers compatible with the cell cultures such as for example PBS. For example first of all a mixture comprising Glusose oxidase and Catalase will be prepared, thereto firstly BSA and then the cross-linking agent, for example GDA, is added.

The present invention also relates to an in vitro method to control the chemical microenvironment of a cell culture and/or a method for mimicking physiological or pathological conditions of the in vivo cells. Such methods will include at least a step wherein the cell line or the primary cells are plated and cultivated in a device such as for example a Petri dish wherein a composition was deposited, preferably a hydrogel as those described herein. According to an embodiment tumour or epithelial cells will be used. Examples of specific cell lines which could be used are MCF7 and MCF10A as shown in greater detail in the experimental section.

As shown previously in the description the compositions including the polymeric matrixes, the hydrogels and the devices described herein advantageously could be used in in vitro methods for screening candidate compounds for example as drugs to evaluate the compound effect on a determined cell line.

The following examples are provided to ease the comprehension of the invention, and they are not meant and they must not be interpreted in any way as limiting the invention described in the following claims.

All cell lines used in the experimentation shown in the present patent application are lines which can be purchased and available on the market.

Examples 1.1 Hydrogel with GOx and CAT

Glucose oxidase—GOx—is an enzyme of the family of oxidoreductases which catalyses the following reaction:

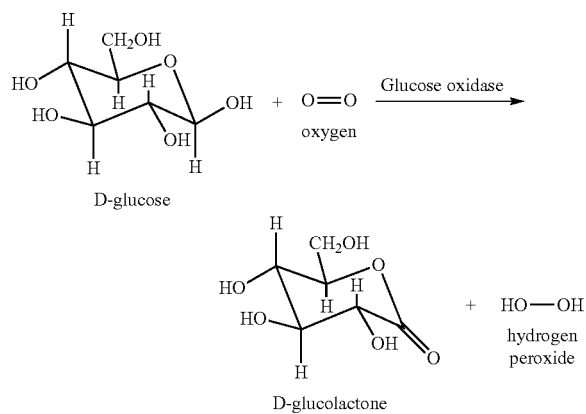

Hydrogen peroxide is a very reactive molecule, toxic for cells, for this reason the above reaction was coupled to that of Catalase—CAT—, another very important oxidoreductase in the biological systems, which transforms the ROS species produced in water. Net of both reactions two oxygen molecules are transformed into two molecules of water plus one of oxygen, which will return into the cycle of Glucose oxidase. The hydrogel consumes oxygen in presence of glucose, the glucose is present in cell culture means as fundamental substrate of the cell metabolism. The enzymes are proteins and as such they have different reactive functional groups, such as aminoacid groups (—NH2) and carboxylic groups (—COOH) which can easily bind covalently to suitable agents such as glutaraldeide (FIG. 1). Glutaraldeide is a small colourless molecule, liquid at room temperature and soluble in any proportion both in water and in alcohol; structurally it is a linear dialdehyde with five carbon atoms, exactly the aldehyde groups give it these high reactivity features. The optimum concentrations were evaluated so as to favour the interactions between enzyme and GDA with respect to intramolecular reactions (low concentrations of enzyme) and to avoid both that the enzyme escapes from the gel (low concentrations of GDA) and that the enzyme becomes insoluble due to the high number of cross-links (high concentrations of GDA). The enzymatic activity is inversely proportional to the used concentrations of GDA as the high number of cross-links distorts the active conformation of the enzyme. Glutaraldeide is a toxic substance, but in previous studies as well as in our experiments it was observed that in the used concentrations it does not create problems to the cell cultures; besides, it is a fixing agent, but as observed in some videos in time lapse performed to evaluate the cell motion, it can be stated that this function is not carried out in these concentrations and that the cells are then free to move on the gel itself without remaining stuck. In the gel formation the use of a solution of Bovine Serum Albumin (BSA) as protective and gelling matrix is fundamental to avoid the denaturation of the enzymes during gelification. Moreover BSA existing in huge concentrations enters the hydrogel network and GDA creates several cross-links between the BSA molecules, and between BSA molecules and enzyme molecules: in this way the concentration of the enzymes can be reduced or increased to the quantities required by the device without the risk that the enzyme is not fixed in the gel if existing at very low concentrations, moreover the presence of BSA decreases the possibility of intermolecular cross-links in the enzymes which can denature them by inhibiting the activity thereof.

1.2 Electrochemical Probe Microscopy for Evaluating the Gradient of Oxygen Concentration In order to evaluate the concentration gradient of the oxygen generated by the gel in our devices we used the scanning electrochemical microscope, a powerful instrument for evaluating chemical processes in micrometric scales and then useful to characterize the microenvironments of the cell cultures. By using an ultramicroelectrode (UME) it is possible to detect electrochemical processes such as redox processes. The probe (UME) is connected to a system having three engine and three piezoelectric elements, and then it can be moved and positioned in the three Cartesian axes X, Y and Z. Such system allows to solve in space the process measured at UME and then it allows to display the topography and to probe the local chemical reactivity of the substrate. At first, by approaching, one approaches to the substrate, negative feedback mode and the current in case of our analyses decreases gradually as one approaches: it→0 like d→0, wherein d is the distance between the probe and the substrate made of plastic or glass in the specific case. In this way it is possible to select the ideal position for our electrode, quite near to the gel to measure the functionality thereof, but not too much, to avoid to damage it mechanically. At this point by doing a scanning parallel to the substrate, in substrate generation-tip collection (SG-TC) mode the electrode is moved near the surface, dipped in solution, the current passing to UME is recorded for each position on the substrate; what it is observed is a change in current which reflects the concentration change in the species which one is measuring at UME. Both curves and bidimensional images of the current can be obtained depending upon the probe position. The fact of succeeding in evaluating this oxygen gradient is fundamental to be able to correlate the enzyme concentrations to the re-created gradient and to evaluate to which oxygen concentrations the cells which are in a particular position of the device substrate are exposed (that is the microenvironment of each single cell is measured), by establishing the parameters in order to create an in vitro model similar to the tumour model or model of physiological/pathological tissue or niche (ex. stem niche) which one wishes to mimic.

2.1 Preparation of the Hydrogel with GOx and CAT

| Table of reagents | | |
|---|---|---|
| Reagents | Concentration | MSDS cards |
| PBS for stock solution | | R36 irritating for eyes |
| BSA stock solution | 62.5 mg/ml in PBS | not dangerous |
| Catalase | 32 mg/ml in stock solution | not dangerous |
| Glucose oxidase | 16 mg/ml in stock solution | H334 - allergic symptoms, asthma or respiratory difficulties by inhalation |
| Glutaraldeide | | harmful by ingestion and toxic by inhalation, skin sensitisation. Toxic for aquatic organisms |

After having prepared the solutions of Catalase and Glucose oxidase they are mixed in ratio 1:1 in a solution containing BSA a quantity of glutaraldeide (water by 25%) equal to 1.38% of the total final volume is added. For preparing white only BSA is used with the same percentage of glutaraldeide. Glutaraldeide is to be added only just before the use of gel since the solution will tend to gel quickly. The Glucose oxidase (type X) is of *Aspergillus Niger* fungus whereas the Catalase of bovine liver. All used compounds were purchased from Sigma Aldrich.

2.2 SECM Instrumentation Used for Measurements

The instrument used for measuring the oxygen gradient is the probe scanning electrochemical microscope "CH Instrument Texas" model CHI B910.

2.3 Analysis of Cell Growth in the Substrates with GOx and CAT

In order to evaluate the way in which our hydrogel influenced the cell growth, both MCF7 and MCF10A, were cultivated:
 i) in presence of hydrogel with the enzymes
 ii) in presence of hydrogel without enzymes, the white
 iii) in absence of hydrogel
 and the cell count was performed by using a colorimetric marker of cell viability at 24, 48 and 72 hours. The comparison between i) and ii) is fundamental for evaluating if the cells suffer from the gradient created by the enzymes, the comparison between ii) and iii) was made to evaluate if the base composition of the gel should be somewhat toxic for cells.

On each chamber cells will be plated and cultivated; the colorimetric assay of cell viability in periods of time of 24 h, 48 h and 72 h (a multiwell per day) will be made, therefrom the cell growth curve will be then obtained. The experiments is repeated both for MCF10A and for MCF7 The plating is performed in several steps of:
 Splitting (Dish 10 cm)
 Putting 1 ml of medium in a falcon 15
 Removing the medium and washing with 5 ml of PBS
 1 ml of trypsin* and in incubator for 5 minutes
 Resuming the cells with trypsin and putting them in falcon 15
 Resuming the cells remained on the dish with 2 ml of medium
 Adding 3 ml of medium and centrifuging
 Removing the supernatant and re-suspending the "pellet" in few ml of medium (depending upon how many cells are available)
 Cell count
 dilution 1:2 cells: PBS in 64-chamber (about 20 µL of the suspension of cells for this procedure are used)
 dilution 1:2 solution in PBS:ERYTHROSINEB
 Putting 10 µl in so-prepared solution in Burker chamber and proceeding with the count at the optical microscope.
 The total cells are calculated with the following formula:

$$M \times V \times 10^{-4} \times F.D._{PBS} \times F.D._{EB}$$

wherein M is the average of the cell counts of cells of Burcker chamber, V is the volume wherein the pellet of cells was re-suspended, F.D. are the dilution factors.
 Plating
 Once performed the count, one decides how many cells are to be plated
  Picking up the adequate quantity of cell solution and suspending it in adequate nml of medium
  Re-distributing in all chambers of the multiwell or of used 3.5-cm wide Petri.
 *trypsin favours the rupture of the peptide bonds allowing the adhesion of the cells to the petri.

After plating the cell count at 24 h, 48 h and 72 h is performed by always proceeding as the items "splitting" and "cell count" for each one of the 6 chambers of the multiwell; the only variation will be the quantities of PBS and trypsin to be used, as it is a dish with width of 3.5 cm and not 10 cm and the quantities will be suitably compared. In other multiwells the cells were plated in presence of hydrogel and white and they were monitored with optical microscope equipped with microincubator in time-lapse for 18/24 hours, so as to evaluate the cell shifting with respect to the gel.

2.4 Cell Growth Density with Respect to the Oxygen Gradient

Several plates (dish) were prepared, wherein cells MCF10A and MCF7 could be plated subsequently. Cells were fixed after 2 days of culture, before reaching confluence, to do the relative count thereof in all points and to evaluate the growth at different distances from the gel.

3. Analysis of Results

Figure 3:
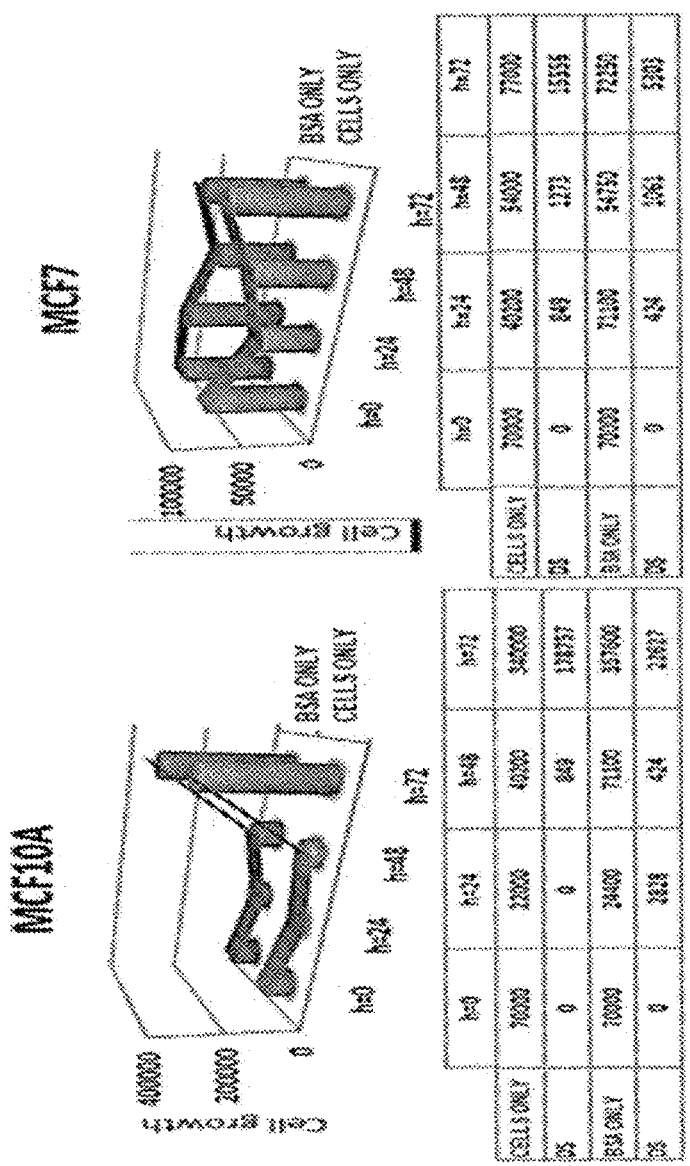
FIG. 3: growth curves of cells MCF10A and MCF7 on control plates and plates modified with the not active (not containing enzymes) protein matrix. The curves show the biocompatibility and the absence of toxicity of the used matrix.

FIG. 3: Growth curves of cells MCF10A and MCF7 on control plates and plates modified with the not active (not containing enzymes) protein matrix. The curves show the biocompatibility and the absence of toxicity of the used matrix.

The biocompatibility and the absence of toxicity of the protein hydrogel used to incorporate the enzymes which generate the gradient was tested by means of cell culture and cell viability test with erythrosine B. Cell counts at 24 h, 48 h and 72 h of culture were performed and the cell growth is not influenced by the presence of the matrix on the surface of the culture plate.

The oxygen gradient was characterized with micrometric resolution by means of scanning electrochemical microscopy.

Figure 4:
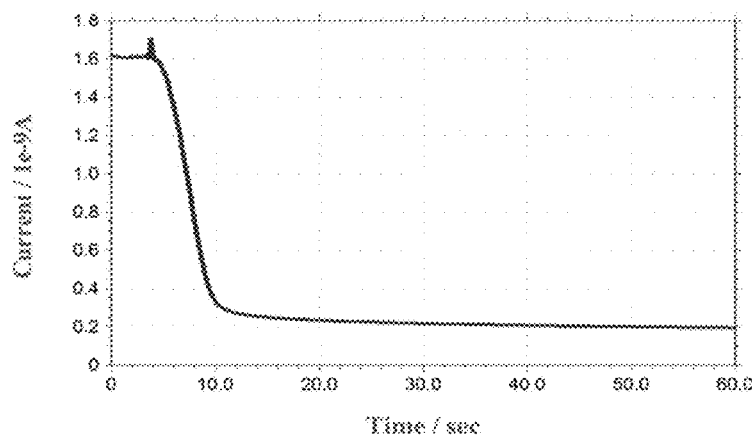
FIG. 4. Amperometry recorded at UME (Pt 10 μm) positioned at few tens of micrometres from the active gel generating hypoxia, E=−0.7V vs Ag/AgCl in PBS. At about 4 s glucose at a concentration 1 mM was added.

The curve in FIG. 4 shows the amperometry recorded at the potential of oxygen reduction equalling to −0.7V vs Ag/AgCl (3M KCl), the working electrode is UME by SECM which is kept few tens of micrometres from the active gel on the petri. The recorded current is directly proportional to the oxygen concentration. At about 4 seconds from the curve beginning a concentration of 1 mM of glucose was added to PBS (analysis solution) was added; after such addition at the level of active matrix the glucose oxidation process starts which is associated to the reduction of oxygen to hydrogen peroxide (converted to water and oxygen by catalase). On the whole the oxygen is consumed and as it is observed from the curve the current decreases drastically after adding glucose due to the sudden decrease in the oxygen concentration (the currents recorded after 20 s correspond to a local oxygen concentration equal to zero), it is to be noted that the current and then the oxygen concentration remains stable in time in the particular localization analysed by the microelectrode.

FIG. 4. Amperometry recorded at UME (Pt 10 μm) positioned few tens of micrometres from the active gel generating hypoxia, E=−0.7V vs Ag/AgCl in PBS. At about 4 s glucose at a concentration of 1 mM was added.

Figure 5:
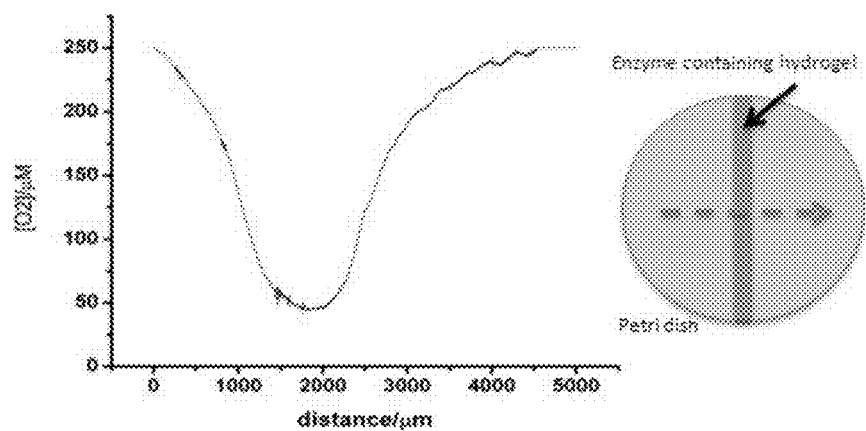
FIG. 5. Scanning curve at UME on a strip of active matrix for producing hypoxia, the direction is perpendicular to the active strip and the electrode is kept at a constant height from the plate whereon the active matrix is placed. E=−0.7V vs Ag/AgCl (3M KCl) in 1 mM glucose in PBS.

FIG. 5 shows a scanning curve wherein UME is kept at a height of ≈25 μm from the gel surface and it is scanned on a gel strip having a thickness of some hundreds of micrometres along a line perpendicular to the direction of the gel strip and parallelly to plate plane whereon the active matrix was placed. From the figure it can be seen that hypoxia is marked in proximity of the strip of active matrix and that the gradient of the concentration generated thereby has a length of some hundreds of micrometres according to the gradient structuration found in vivo and caused by the distance existing between different capillaries and blood vessels.

FIG. 5. Oxygen concentration detected by means of a scanning curve of UME on a strip of active matrix for generating hypoxia, the direction is perpendicular to the active strip and the electrode is kept at a constant height from the plate thereon the active matrix is placed. E=−0.7V vs Ag/AgCl (3M KCl) in 1 mM glucose in PBS.

Figure 6:
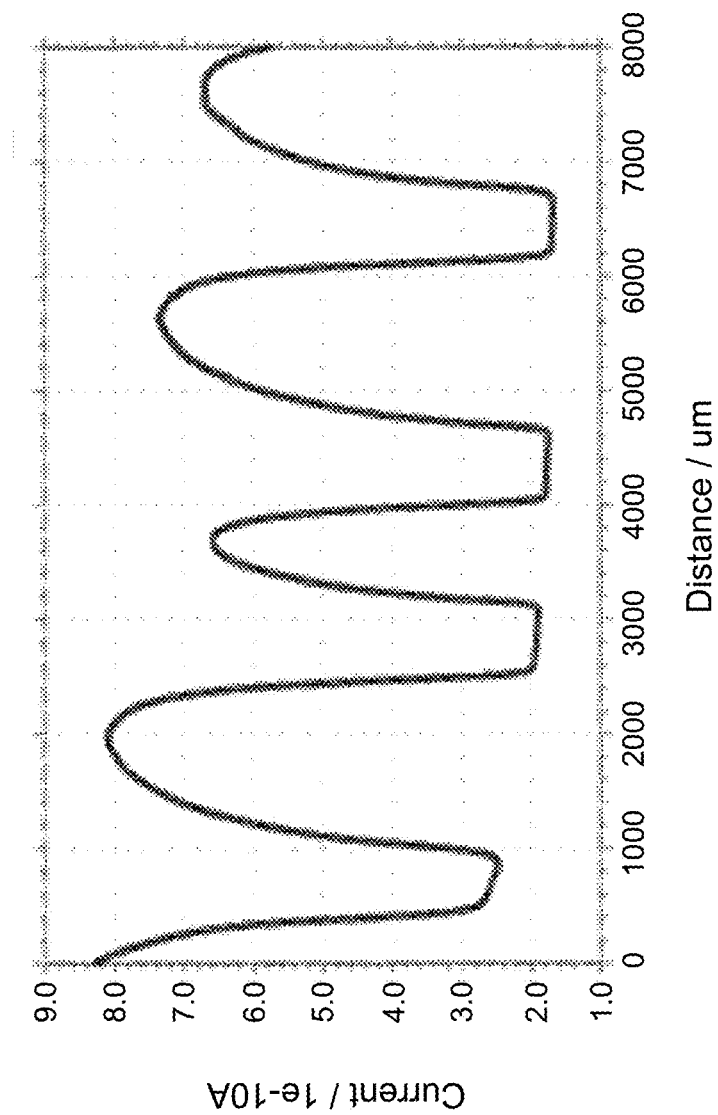
FIG. 6. Scanning curve of UME (Pt 10 μm) on a plate modified by strips of active matrix placed at a distance of 1-1.5 mm from one another. E=−0.7V vs Ag/AgCl (3M KCl) in a solution of 1 mM glucose in PBS.

FIG. 6 shows a scanning curve with UME parallel to the surface of the culture plate in a direction perpendicular to four strips of active matrix placed at a distance of 1-1.5 mm from one another. The surface modification re-creates hypoxic areas and the related oxygen gradients with a structure similar to the one found in vivo and due to the distribution of the capillaries.

FIG. 6. Scanning curve of UME (Pt 10 μm) on a plate modified by strips of active matrix placed at a distance of 1-1.5 mm from one another. E=−0.7V vs Ag/AgCl (3M KCl) in a solution of 1 mM glucose in PBS.

Figure 7:
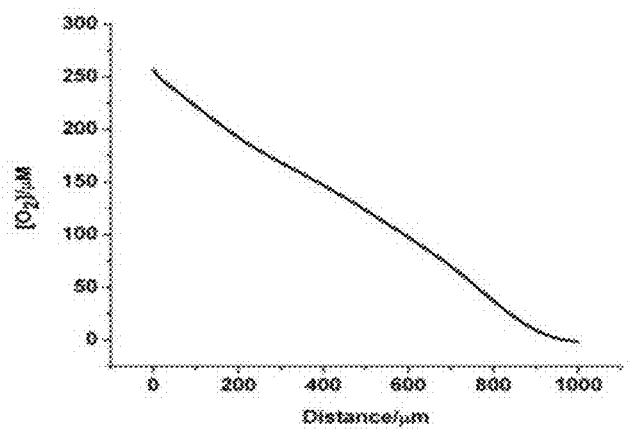
FIG. 7. Approach curve in proximity of the gel performed in presence of glucose 1 mM in PBS, at potential=−0.6 V and maximum speed of 50 μm/s, with Pt UME 10 μm and reference electrode Ag/AgCl (3 M KCl).

FIG. 7 shows an approach curve (the currents were converted into oxygen concentrations) recorded by approaching UME to the active gel from the other one in a direction perpendicular thereto. It can be noted that the gradient of oxygen concentration spreads in the middle even in the direction perpendicular to the plate surface, such feature demonstrates the 3D structuration concept of the gradient. It is noted that at the end of the approach, few tens of microns from the gel, null concentrations of $O_2$ are obtained.

FIG. 7 Approach curve in proximity of the gel performed in presence of glucose 1 mM in PBS, a potential=−0.6 V and maximum speed of 50 μm/s, with Pt UME 10 μm and reference electrode Ag/AgCl (3 M KCl).

Figure 8:
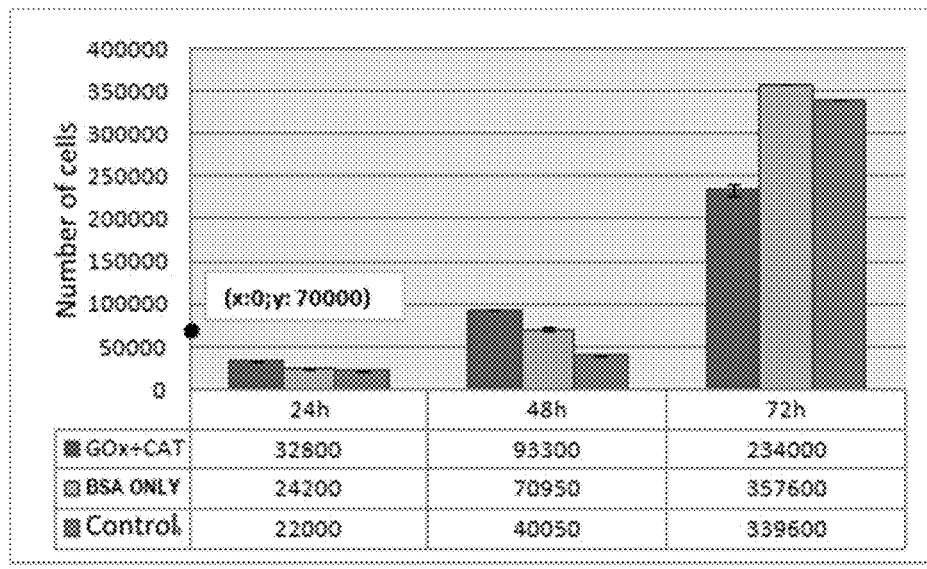
FIG. 8: Growth curves by using erythrosine B for the viability of cells MCF10A on control plates and plates modified with the not active (only BSA) and active (containing Gox and CAT) proteic matrix. The curve shows the biocompatibility and the absence of toxicity of the used matrix. Furthermore, the effect on the growth of the chemical gradient existing in the active plates is highlighted.
Figure 9:
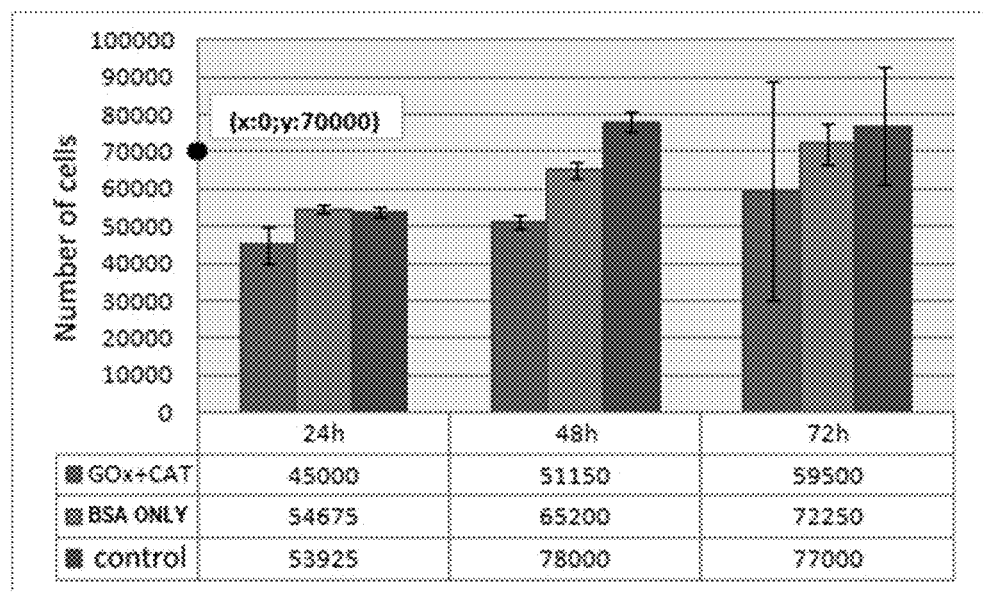
FIG. 9: Growth curves by using erythrosine B for the viability of cells MCF10A on control plates and plates modified with the not active (solo BSA) and active (containing Gox and CAT) protein matrix. The curve shows the biocompatibility and the absence of toxicity of the used matrix. Moreover the effect on the growth of the chemical gradient existing in the active plates is highlighted.

Once characterized the oxygen gradients re-created by the device we cultivated in such engineered plates cells MCF10A and MCF7. FIG. 8 and FIG. 9 show the growth curves of cells MCF10A and MCF7, respectively, it is observed that the presence of a strip of active material in the plate surface centre modifies the growth of the cells.

FIG. 8: Growth curves by using erythrosine B for the viability of cells MCF10A on control plates and plates modified with the not active (only BSA) and active (containing Gox and CAT) protein matrix. The curve shows the biocompatibility and the absence of toxicity of the used matrix. Moreover the effect on the growth of the chemical gradient existing in the active plates is highlighted.

FIG. 9: Growth curves by using erythrosine B for the viability of cells MCF7 on control plates and plates modified with the not active (only BSA) and active (containing Gox and CAT) protein matrix. The curve shows the biocompatibility and the absence of toxicity of the used matrix. Moreover the effect on the growth of the chemical gradient existing in the active plates is highlighted.

Figure 10:
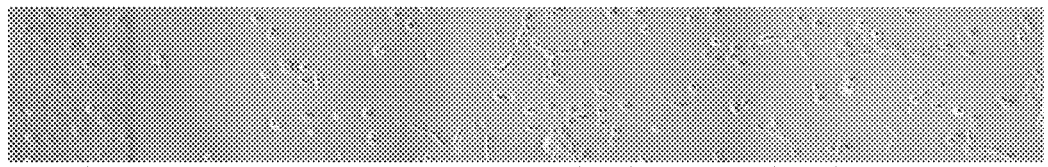
FIG. 10. Optical image of cells MCF10A cultivated for 24 h in presence of active hydrogel with enzymes (on the left).

FIG. 10 shows the optical image taken after 48 hours of culture of cells MCF10A in a plate engineered with the active hydrogel (visible on the left of the image). It is observed that the cells grow with a gradient density in response to the oxygen gradient existing in the culture medium in proximity of the gel. Such gradient is not present in the plates modified with not active control gel (FIG. 11).

FIG. 10. Optical image of cells MCF10A cultivated for 24 h in presence of active hydrogel with enzymes (on the left).

Figure 11:
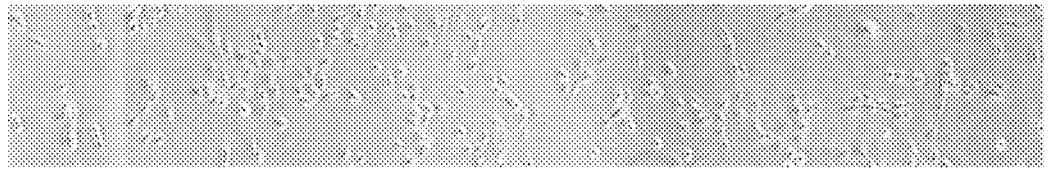
FIG. 11. Optical image of cells MCF10A cultivated for 24 h in presence of not active hydrogel (on the left).

FIG. 11. Optical image of cells MCF10A cultivated for 24 h in presence of not active hydrogel (on the left).

Figure 12:
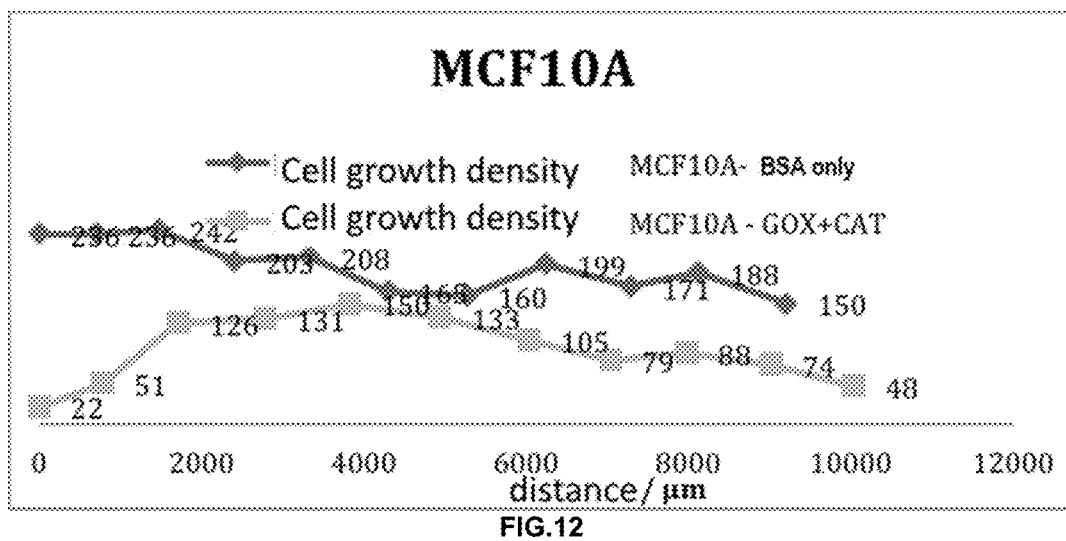
FIG. 12. Cell growth density depending upon the distance of the cells MCF10A from the hydrogel, comparison with gel in presence of enzymes and with control gel. The course of the cell density is homogeneous in the control plates, contrary to those in presence of gradient wherein the area with lower density is observed in proximity of the hypoxic area.

FIG. 12 shows the cell density depending upon the distance from the active and control gel (FIGS. 10 and 11) and then in the oxygen gradient shown in FIG. 5 or in absence of gradient.

FIG. 12. Cell growth density depending upon the distance from the hydrogel of the cells MCF10A, comparison with gel in presence of enzymes and with control gel. The course of the cell density is homogeneous in the control plates, contrary to those in presence of gradient wherein the area with lower density is observed in proximity of the hypoxic area.

Figure 13:
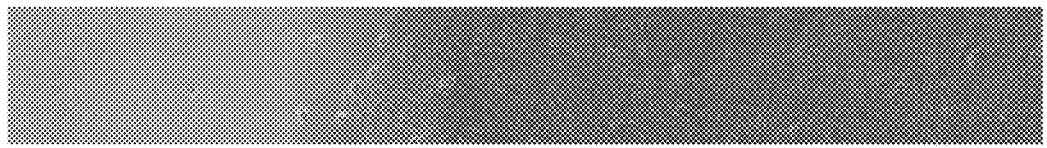
FIG. 13. Optical image of cells MCF10A cultivated for 24 h in presence of not active hydrogel (on the left).

FIG. 13 shows the taken optical image of culture to confluence of MCF10A in a plate engineered with the active hydrogel (visible on the left of the image). It is observed that the cells grow with a gradient density in response to the oxygen gradient existing in the culture medium in proximity of the gel. Such gradient is not present in the plates modified with not active control gel (FIG. 14).

FIG. 13. Optical image of cells MCF10A cultivated for 24 h in presence of not active hydrogel (on the left).

Figure 14:
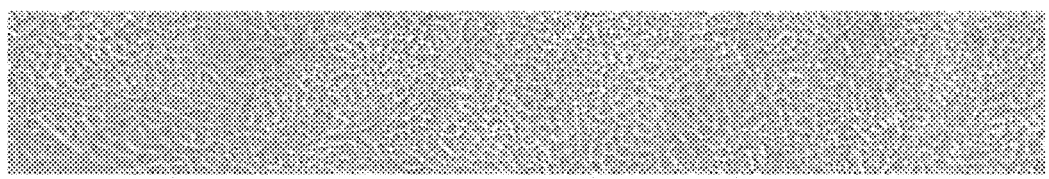
FIG. 14. Optical image of cells MCF10A cultivated for 24 h in presence of not active hydrogel (on the left).

FIG. 14. Optical image of cells MCF10A cultivated for 24 h in presence of not active hydrogel (on the left).

Figure 15:
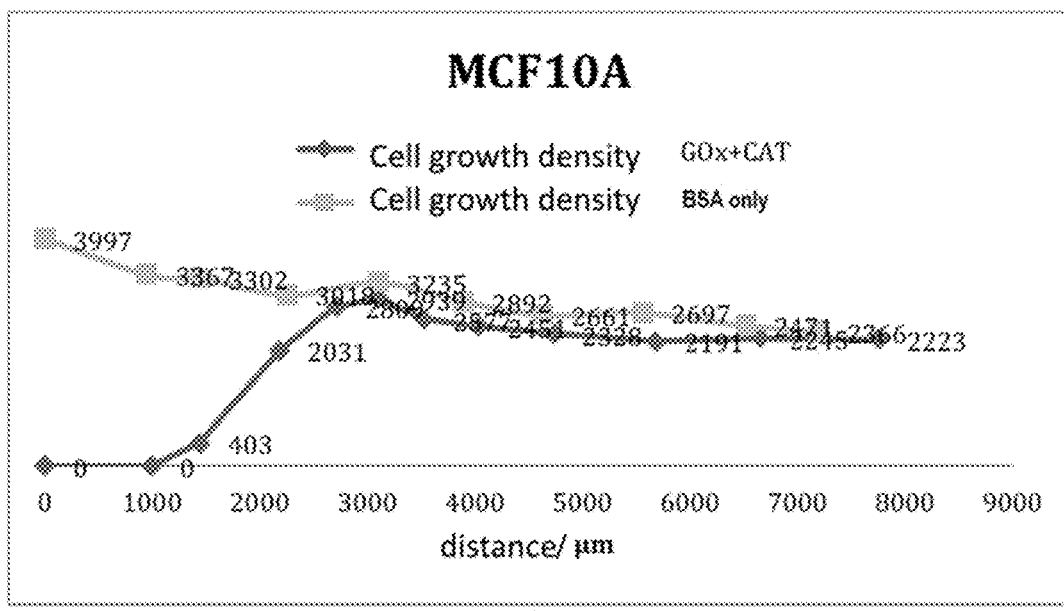
FIG. 15. Cell growth density depending upon the distance from the hydrogel of the cells MCF10A, in confluence comparison with gel in presence of enzymes and with control gel. The course of the cell density is homogeneous in the control plates, contrary to those in presence of gradient wherein the area with lower density is observed in proximity of the hypoxic area.

FIG. 15. Cell growth density depending upon the distance from the hydrogel of the cells MCF10A, to confluence comparison with gel in presence of enzymes and with control gel. The course of the cell density is homogeneous in the control plates, contrary to those in presence of gradient wherein the area with lower density is observed in proximity of the hypoxic area.

Figure 16:
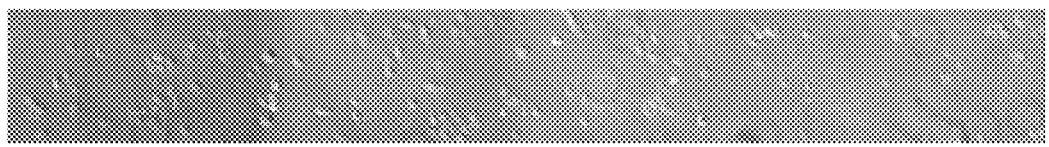
FIG. 16. Optical image of cells MCF7 cultivated for 24 h in presence of active hydrogel with enzymes (on the left).
Figure 17:
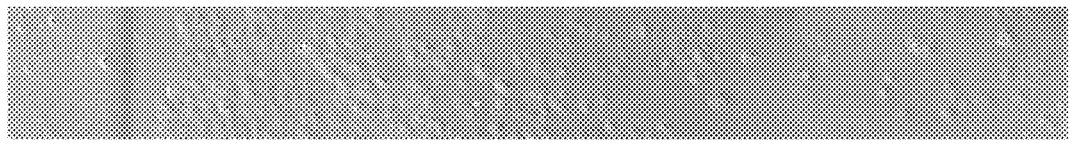
FIG. 17. Optical image of cells MCF7 cultivated for 24 h in presence of not active hydrogel (on the left).

FIG. 16 shows the optical image taken after 48 hours of culture of cells MCF7 in a plate engineered with the active hydrogel (visible on the left of the image). It is observed that the cells grow with a gradient density in response to the oxygen gradient existing in the culture medium in proximity of the gel. Such gradient is not existing in the plates modified with not active control gel (FIG. 17). It is to be noted that in case of MCF7, tumour cells, the cell density is increased in proximity of the oxygen and thus in the hypoxic areas (such situation is similar to the one thereto the cells of tumour tissues are exposed).

FIG. 16. Optical image of cells MCF7 cultivated for 24 h in presence of active hydrogel with enzymes (on the left)

FIG. 17. Optical image of cells MCF7 cultivated for 24 h in presence of not active hydrogel (on the left).

Figure 18:
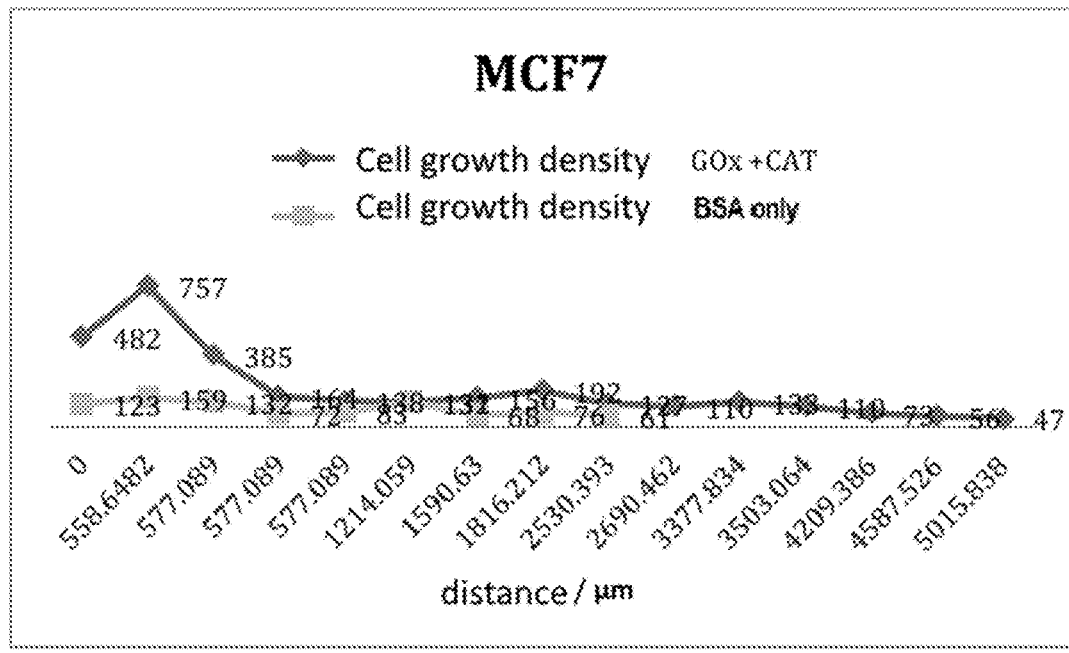
FIG. 18. Cell growth density depending upon the distance from the hydrogel of the cells MCF7, comparison between gel in presence of enzymes and control gel. The course of the cell density is homogeneous in the control plates, contrary to those in presence of gradient wherein the area with higher density is observed in proximity of the hypoxic area.

FIG. 18 shows the cell density depending upon the distance from the active and control gel (FIGS. 16 and 17) and then in the oxygen gradient shown in FIG. 5 or in absence of gradient.

FIG. 18. Cell growth density depending upon the distance from the hydrogel of the cells MCF7, comparison between gel in presence of enzymes and control gel. The course of the cell density is homogeneous in the control plates, contrary to those in presence of gradient wherein the area with higher density is observed in proximity of the hypoxic area. The expression of some proteins of interest of the normal and tumour cells cultivated in control plate and in the engineered ones was investigated by means of Western Blot (FIG. 19) and the results demonstrate the effectiveness of our device in controlling the cell microenvironment and the consequences of such conditions in the cell phenotypes, in particular the effect on the protein HIF-1α, which is active under hypoxic conditions (HIF-1α is found in many cells of tumour tissues), is to be noted. The cells were cultivated in plates modified with a pattern of grids of active or control gel with strips at a distance of 2 mm or 3 mm from one another.

Figure 19:
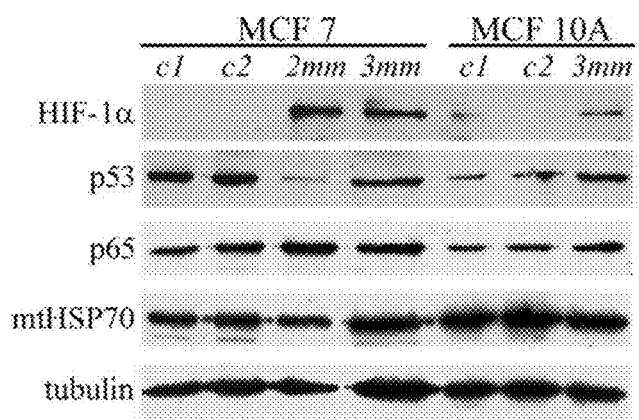
FIG. 19. WB of some proteins of interest expressed by cells MCF10 and MCF7 cultivated in the plates engineered with grids of active gel (at distance of 2 mm or 3 mm between adhering strips) or with control grids.

FIG. 19. WB of some proteins of interest expressed by cells MCF10 and MCF7 cultivated in the plates engineered with grids of active gel (strips at a distance of 2 mm or 3 mm between adjacent strips) or with control grids.

The invention claimed is:

1. An in vitro method to control the chemical microenvironment of a cell culture and/or mimic the physiological or pathological conditions of the cells in vivo, comprising
    depositing, in a container for a cell culture, a
    grid or strip(s) of a composition in the form of a hydrogel comprising a matrix that contains one or more enzymes capable of catalyzing the reduction of oxygen, so that an oxygen gradient is generated under cell cultivation from the region of the container where said hydrogel is deposited to the region of the container where said hydrogel is not deposited;
    wherein said enzymes are covalently bound to said matrix by a cross-linking agent (cross-linker) or are trapped in a polymeric matrix through mechanical and/or electrostatic interactions and wherein said container is a culture plate;
    cultivating a cell line or primary cells in said container.

2. The method according to claim 1 further comprising measuring the oxygen gradient generated by said composition.

3. The method according to claim 1 wherein said cell cultures comprise cancer cells.

4. The method according to claim 1 wherein said cells are epithelial cells.

5. An in vitro method to evaluate the effect of a drug or compound on a physiological or pathological condition comprising
    depositing in a container for a cell culture a grid or strip(s) of a composition in the form of a hydrogel comprising a matrix that contains one or more enzymes capable of catalyzing the reduction of oxygen, so that an oxygen gradient is generated under cell cultivation from the region of the container where said hydrogel is deposited to the region of the container where said hydrogel is not deposited;
    wherein said enzymes are covalently bound to said matrix by a cross-linking agent (cross-linker) or are trapped in a polymeric matrix through mechanical and/or electrostatic interactions and wherein said container is a culture plate;
    depositing said drug or compound in said container; and
    cultivating a cell line in said container.

6. The method according to claim 1, wherein said matrix is a polymeric or protein matrix.

7. The method according to claim 1, wherein said enzyme is selected from Glucose oxidase (GOx), NADPH oxidase, xanthine oxidase, lactate oxidase, cytochrome oxidase or Laccases.

8. The method according to claim 1, wherein said composition further comprises the Catalase enzyme.

9. The method according to claim 1, wherein said cross-linking agent is selected from the group consisting of: glutaraldehyde (GDA), Bis(sulfosuccinimidil) suberate, N-hydroxysuccinimide, formaldehyde, and photoreactive agents.

10. The method according to claim 1, wherein said hydrogel is selected from the group consisting of: silicone hydrogel, polyacrylamides, cellulose, cellulose derivatives, collagen, carboxymethylcellulose, alginate, chitosan, agar, polimacon, hyaluronic acid, and polymethylmethacrylate.

11. The method according to claim 1, wherein the matrix of said hydrogel further comprises the Bovine Serum Albumin (BSA).

12. The method according to claim 1, wherein the polymeric matrix of said hydrogel comprises Glucose oxidase (GOx), Catalase and Bovine Serum Albumin (BSA) covalently bound by Glutaraldehyde.

13. The method according to claim 2, wherein said measuring is performed by means of a scanning electrochemical microscope.

14. The method according to claim 1, wherein said grid is composed of strips of said composition, wherein the distance between adjacent strips is 2 mm or 3 mm.

15. The method according to claim 1, wherein said culture plate is a Petri dish.

* * * * *